United States Patent [19]

Behr et al.

[11] Patent Number: 5,342,965
[45] Date of Patent: Aug. 30, 1994

[54] PROCESS FOR PRODUCING BRANCHED FATS

[75] Inventors: Arno Behr; Hans-Peter Handwerk, both of Duesseldorf, Fed. Rep. of Germany

[73] Assignee: Henkel Kommanditgesellschaft auf Aktien, Duesseldorf, Fed. Rep. of Germany

[21] Appl. No.: 94,121
[22] PCT Filed: Dec. 17, 1991
[86] PCT No.: PCT/EP91/02427
 § 371 Date: Jul. 29, 1993
 § 102(e) Date: Jul. 29, 1993
[87] PCT Pub. No.: WO92/12955
 PCT Pub. Date: Aug. 6, 1992

[30] Foreign Application Priority Data

Jan. 29, 1991 [DE] Fed. Rep. of Germany ....... 4102500

[51] Int. Cl.$^5$ ............................................. C07D 307/60
[52] U.S. Cl. ..................................... 549/233; 549/252
[58] Field of Search ................................. 549/233, 252

[56] References Cited

U.S. PATENT DOCUMENTS 2,569,420 9/1951 Kosmin ............................ 260/404.8

FOREIGN PATENT DOCUMENTS 2828384 1/1979 Fed. Rep. of Germany .
2081274 2/1982 United Kingdom .

OTHER PUBLICATIONS

*The Reaction of Nonconjugated Unsaturated Fatty Acid Esters with Maleic Anhydride*, W. G. Bickford, P. Krauczunas and D. H. Wheeler, Oil and Soap, 18/19, 23–27 (1942).
*Polymerization of Drying Oils. III. Some Observations on Reaction of Maleic Anhydride with Methyl Oleate and Methyl Linoleate*, H. M. Teeter, M. J. Geerts, and J. C. Cowan, J. Am. Oil. Chem. Soc., 25, 158 (1948).
*Autoxidation of Fats. II. Preparation and Oxidation of Methyl Oleate–Maleic Anhydride Adduct*, W. G. Bickford, G. S. Fisher, Lillian Kyame, and C. E. Swift, J. Am. Oil. Chem. Soc., 25, 254 (1948).
*Addition of Maleic Anhydride to Esters of Mono-unsaturated Fatty Acids*, Krister Holmberg and Jan-Allan Johansson, Acta Chem. Scand., B36, 481 (1982).
Fat Sci. Technol., 90, 1 (1988).
*Reaction of Maleic Anhydride with cis-Isolated Unsaturated Fatty Acid Esters*, by Prof. Dr. A. E. Rheineck and Dr. T. H. Khoe, Fette, Seifen, Anstrichmtt., 71, 644 (1969).

Primary Examiner—Cecilia Tsang
Attorney, Agent, or Firm—Ernest G. Szoke; Wayne C. Jaeschke; Norvell E. Wisdom, Jr.

[57] ABSTRACT

Branched fatty substances may be produced by reacting maleic acid anhydride with fatty acids having 16 to 24 carbon atoms and 1, 2, 3, 4, or 5 double bonds, or the esters of such acids, with alcohols containing 1 to 4 carbon atoms, in the presence of at least one rhodium and/or platinum catalyst.

20 Claims, No Drawings

1

PROCESS FOR PRODUCING BRANCHED FATS

FIELD OF THE INVENTION

This invention relates to a process for the production of branched fats by addition of maleic anhydride onto unsaturated fatty acids or esters thereof in the presence of rhodium and/or platinum catalysts.

STATEMENT OF RELATED ART

Branched fats are distinguished from linear fats by lower pour points, lower volatility, better oxidation stability, higher wetting power and easier blendability. Accordingly, they are important raw materials for the production of surface-active compositions, such as for example surfactants, lubricants, rolling and drawing oils, cosmetics, textile and paper auxiliaries [DE-A1-28 28 384].

A proven process for the production of branched fats is the addition of maleic anhydride (MA) onto unsaturated fatty acids or esters thereof ("maleicization"). If monounsaturated fats are used, the reaction takes place as a so-called "ene reaction" [Fat Sci. Technol., 90, 1 (1988)]. If, by contrast, fats containing two or more double bonds are used, a Diels-Alder reaction takes place. Both reactions are carried out in the absence of catalysts at temperatures above 200° C. and lack selectivity [Oil and Soap, 18/19, 23 (1942); J. Am. Oil. Chem. Soc., 25, 254 (1948)].

DESCRIPTION OF THE INVENTION

Object of the Invention

The problem addressed by the present invention was to provide a process for the production of branched fats which would be free from the disadvantages mentioned above.

SUMMARY OF THE INVENTION

The present invention relates to a process for the production of branched fats by addition of maleic anhydride onto unsaturated fatty acids or lower alkyl esters thereof, characterized in that maleic anhydride is reacted with fatty acids containing 16 to 24 carbon atoms and 1, 2, 3, 4 or 5 double bonds or esters thereof with alcohols containing 1 to 4 carbon atoms in the presence of at least one rhodium and/or platinum catalyst.

It has surprisingly been found that the maleicization of fatty acids or fatty acid esters in the presence of rhodium salts gives high yields of addition products, even at comparatively low temperatures.

Suitable starting materials for the production of the branched fats are fatty acids containing 16 to 24 carbon atoms and 1, 2, 3, 4 or 5 double bonds and esters thereof with alcohols containing 1 to 4 carbon atoms. Typical examples are palmitoleic acid, oleic acid, elaidic acid, petroselic acid, chaulmoogric acid, ricinoleic acid, linoleic acid, linolenic acid, gadoleic acid, arachidonic, erucic acid or clupanodonic acid and methyl, ethyl, propyl or butyl esters thereof. Oleic acid or oleic acid methyl ester is preferably used.

As usual in oleochemistry, the fatty acids or their esters may also be present in the form of the technical cuts which are formed in the pressure hydrolysis or transesterification of natural fats and oils, such as for example cottonseed oil, peanut oil, rapeseed oil, linseed oil, soybean oil, coriander oil, sunflower oil, chaulmoogra oil, beef tallow or fish oil. Fatty acid fractions predominantly containing unsaturated fatty acids, i.e. more than 50% by weight unsaturated fatty acids in addition to saturated fatty acids, may also be used in the process according to the invention.

The maleic anhydride and the unsaturated fatty acids or their esters may be used in a molar ratio of 1:1 to 4:1 and preferably in a molar ratio of 2:1.

The rhodium catalysts may be homogeneous or heterogeneous, i.e. may be soluble or insoluble in the reaction mixture. In the context of the process according to the invention, homogeneous rhodium catalysts, which are preferably used, are the halides, acetyl acetonates, acetates and formates of rhodium in its oxidation state III. Mixtures of the salts mentioned may also be used. Suitable heterogeneous catalysts are elemental rhodium on inorganic support materials, for example active carbon.

DESCRIPTION OF PREFERRED EMBODIMENTS

Platinum catalysts are understood to be the halides, acetyl acetonates, acetates and formates of platinum in its oxidation states II and IV.

The rhodium and/or platinum catalysts may be used in concentrations of 0.005 to 10% by weight, based on the maleic anhydride. In order to achieve a high reaction rate, a satisfactory yield of addition products and high process economy, it has proved to be optimal to carry out the reaction in the presence of 0.01 to 2% by weight of the rhodium and/or platinum catalyst, based on the maleic anhydride.

The addition of the maleic anhydride onto the unsaturated fatty acids or their esters may take place at temperatures in the range from 50° to 175° C. In order to ensure a high reaction rate and a satisfactory yield of addition products, it has proved to be optimal to carry out the reaction at temperatures of 90° to 150° C.

To carry out the reaction, it is sufficient initially to introduce the maleic anhydride, the fatty acid or ester and catalyst and to heat them with stirring for 1 to 48 hours and preferably for 8 to 24 hours. In one particular embodiment of the invention, the addition reaction may also be carried out in the presence of a solvent, for example chloroform, 1,2-dichloropropane, isooctane, dioxane, dimethyl formamide, propylene carbonate, ethyl acetate or acetonitrile.

A number of isomeric, cyclic or acyclic products can be formed by the addition of maleic anhydride onto the unsaturated fatty acids or their esters. Where oleic acid or oleic acid ester is used, it may be assumed that addition products of MA are largely formed in the adjacent position to the double bond of the fatty acid component [J. Am. Oil. Chem. Soc., 25, 158 (1948); Fette, Seifen, Anstrichmitt., 71, 644 (1969); Acta Chem. Scand., B36, 481 (1982)].

The branched fats obtainable by the process according to the invention have emulsifying properties and are suitable, for example, for the production of lubricants.

The following Examples are intended to illustrate the invention without limiting it in any way.

EXAMPLES

Example 1

28.2 g (0.1 mole) of technical oleic acid (Edenor® F-TiO$_5$, iodine value 98, a product of Henkel KGaA) and 19.6 g (0.2 mole) of maleic anhydride were introduced into a 100 ml three-necked flask equipped with a stirrer and reflux condenser, followed by the introduction of 0.7 g (2.5 mmole) of rhodium trichloride trihydrate. The reaction mixture was heated to 110° C. and stirred for 24 h. According to analysis of the reaction product by gel permeation chromatography, the yield of addition products amounted to 37% of the theoretical.

The unreacted starting materials were removed by vacuum distillation (120° C./0.2 torr) and the main product fraction was identified by IR and $^{13}$C-NMR spectroscopy. The results are set out in Tables 1 and 2.

TABLE 1

| IR spectrum | |
|---|---|
| Vibration band cm$^{-1}$ | Assignment |
| 921 | C—O—C bond |
| 1785 | Cyclic anhydride structure |
| 1843 | Cyclic anhydride structure |
| 1863 | Cyclic anhydride structure |

TABLE 2

| $^{13}$C—NMR spectrum | |
|---|---|
| Chemical shift ppm | Assignment |
| 174.0 | Ester carboxylate group |
| 173.8 | Saturated anhydride structure |
| 171.7 | Saturated anhydride structure |
| 164.5 | Unsaturated anhydride structure |
| 163.1 | Unsaturated anhydride structure |

Example 2

The procedure was as described in Example 1, except that the reaction was carried out at 130° C. and not 110° C. The yield of addition products amounted to 68% of theoretical.

Example 3

28.2 g of technical oleic acid, 19.6 g of maleic anhydride and 1.0 g (2.5 mmole) of rhodium tris(acetylacetonate) were reacted as in Example 1. The yield of addition products amounted to 49% of the theoretical.

Example 4

28.2 g of technical oleic acid, 19.6 g of maleic anhydride and 0.6 g (1.25 mmole) of rhodium bisacetate dimer were reacted as in Example 1. The yield of addition products amounted to 58% of the theoretical.

Example 5

29.7 g (0.1 mole) of technical oleic acid methyl ester (Edenor MeTiO$_5$, iodine value 97, a product of Henkel KGaA), 19.6 g of maleic anhydride and 0.7 g (2.5 mmole) of rhodium trichloride trihydrate were reacted as in Example 1. The reaction was carried out at 150° C. The yield of addition products amounted to 81% of the theoretical.

Example 6

28.2 g of technical oleic acid, 19.6 g of maleic anhydride and 2.6 mg (0.01 mmole) of rhodium trichloride trihydrate were reacted as in Example 1 at a temperature of 150° C. The yield of addition products amounted to 75% of the theoretical.

Example 7

28.2 g of technical oleic acid, 19.6 g of maleic anhydride and 5.3 mg (0.02 mmole) of rhodium trichloride trihydrate were reacted as in Example 1 at a temperature of 150° C. The yield of addition products amounted to 78% of the theoretical.

Example 8

28.2 g of technical oleic acid, 19.6 g of maleic anhydride and 0.7 g (2.5 mmoles) of platinum dichloride were reacted for 24 h at 110° C. as in Example 1. The yield of addition products amounted to 40% of the theoretical.

Example 9

28.2 g of technical oleic acid, 19.6 g of maleic anhydride and 1.3 g (2.5 mmoles) of hexachloroplatinic acid were reacted for 24 h at 110° C. as in Example 1. The yield of addition products amounted to 64% of the theoretical.

Example 10

28.2 g of technical oleic acid, 19.6 g of maleic anhydride and 5.1 g of a heterogeneous rhodium/active carbon catalyst containing 5% by weight of rhodium (corresponding to 2.5 mmoles of rhodium) were reacted for 24 h at 110° C. as in Example 1. The yield of addition products amounted to 43% of the theoretical.

The invention claimed is:

1. A process for the production of branched fats by addition of maleic anhydride onto unsaturated fatty acids or lower alkyl esters thereof, maleic anhydride is reacted with fatty acids having 16 to 24 carbon atoms and 1, 2, 3, 4 or 5 double bonds, or with esters thereof with alcohols having 1 to 4 carbon atoms, in the presence of at least one rhodium or platinum catalyst.

2. A process as claimed in claim 1, wherein oleic acid is reacted with the maleic anhydride.

3. A process as claimed in claim 1, wherein oleic acid methyl ester is reacted with the maleic anhydride.

4. A process as claimed in claim 3, wherein rhodium halides, acetyl acetonates or acetates are used as the catalyst.

5. A process as claimed in claim 4, wherein the maleic anhydride and the fatty acids or their lower alkyl esters are used in a molar ratio of 1:1 to 4:1.

6. A process as claimed in claim 5, wherein the rhodium or platinum catalyst is used in concentrations of 0.005 to 10% by weight, based on the maleic anhydride.

7. A process as claimed in claim 6, wherein the reaction is carried out at temperatures of 90° to 175° C.

8. A process as claimed in claim 2, wherein rhodium halides, acetyl acetonates or acetates are used as the catalyst.

9. A process as claimed in claim 8, wherein the maleic anhydride and the fatty acids or their lower alkyl esters are used in a molar ratio of 1:1 to 4:1.

10. A process as claimed in claim 9, wherein the rhodium or platinum catalyst is used in concentrations of 0.005 to 10% by weight, based on the maleic anhydride.

11. A process as claimed in claim 10, wherein the reaction is carried out at temperatures of 90° to 175° C.

12. A process as claimed in claim 1, wherein rhodium halides, acetyl acetonates or acetates are used as the catalyst.

13. A process as claimed in claim 12, wherein the maleic anhydride and the fatty acids or their lower alkyl esters are used in a molar ratio of 1:1 to 4:1.

14. A process as claimed in claim 13, wherein the rhodium or platinum catalyst is used in concentrations of 0.005 to 10% by weight, based on the maleic anhydride.

15. A process as claimed in claim 14, wherein the reaction is carried out at temperatures of 90° to 175° C.

16. A process as claimed in claim 3, wherein the maleic anhydride and the fatty acids or their lower alkyl esters are used in a molar ratio of 1:1 to 4:1.

17. A process as claimed in claim 16, wherein the rhodium or platinum catalyst is used in concentrations of 0.005 to 10% by weight, based on the maleic anhydride.

18. A process as claimed in claim 17, wherein the maleic anhydride and the fatty acids or their lower alkyl esters are used in a molar ratio of 1:1 to 4:1.

19. A process as claimed in claim 2, wherein the rhodium or platinum catalyst is used in concentrations of 0.005 to 10% by weight, based on the maleic anhydride.

20. A process as claimed in claim 19, wherein the reaction is carried out at temperatures of 90° to 175° C.

* * * * *